(12) United States Patent
Knight et al.

(10) Patent No.: US 7,725,183 B1
(45) Date of Patent: May 25, 2010

(54) IMPLANTABLE STIMULATION DEVICE EQUIPPED WITH A HARDWARE ELASTIC BUFFER

(75) Inventors: Curtis A. Knight, Santa Clara, CA (US); April Pixley, Los Altos, CA (US); Erica Lundmark, Los Altos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1098 days.

(21) Appl. No.: 11/351,772

(22) Filed: Feb. 10, 2006

(51) Int. Cl.
*A61N 1/00* (2006.01)
(52) U.S. Cl. .......................................... 607/9
(58) Field of Classification Search .............. 607/9, 607/17; 451/41; 398/79; 714/773
See application file for complete search history.

(56) References Cited

U.S. PATENT DOCUMENTS

| | | | |
|---|---|---|---|
| 5,535,226 A * | 7/1996 | Drake et al. ................ | 714/773 |
| 5,918,242 A | 6/1999 | Sarma et al. ................... | 711/5 |
| 6,193,585 B1 * | 2/2001 | Tanabe et al. ................. | 451/41 |
| 6,907,198 B2 * | 6/2005 | Nishimura .................... | 398/79 |
| 2005/0027322 A1 * | 2/2005 | Warkentin .................... | 607/17 |

OTHER PUBLICATIONS

"VLSI Cores QDR-SRAM Controller", 2003, Mistral Software PVt. Ltd. www.mistralsoftware.com, 2 pages.

* cited by examiner

*Primary Examiner*—George Manuel
(74) *Attorney, Agent, or Firm*—Steven M. Mitchell

(57) ABSTRACT

An implantable cardiac stimulation device is equipped with a hardware elastic buffer. In an exemplary device, the hardware elastic buffer comprises SRAM and a SRAM controller. The device optionally includes averaging, concatenating, filling and/or other features.

39 Claims, 9 Drawing Sheets

EXEMPLARY ARRANGEMENT
400

READ DATA
410

| Time 1: | Time 2: | Time 3: |
|---|---|---|
| Data N | Data N+1 | Data N+N |
| Data N-1 | Data N | Data N+N-1 |
| Data N-2 | Data N-1 | Data N+N-2 |
| Data N-3 | Data N-2 | Data N+N-3 |
| ... | ... | ... |
| Data 1 | Data 2 | Data N+1 |

READ VALUES VIA REGISTER
(ORDERED BY ENTRY ORDER)

EXEMPLARY LOGIC
430

PAIRED COLUMNS ARE
DIFFERENT TIME POINTS

STORED VALUES
(ORDERED BY ADDRESS)

| Time 1: | Time 2: | Time 3: |
|---|---|---|
| Data 1 | Data N+1 | Data N+1 |
| Data 2 | Data 2 | Data N+2 |
| Data 3 | Data 3 | Data N+3 |
| Data 4 | Data 4 | Data N+4 |
| ... | ... | ... |
| Data N | Data N | Data N+N |

STORED DATA
420

Fig. 4

IMPLANTABLE STIMULATION DEVICE EQUIPPED WITH A HARDWARE ELASTIC BUFFER

TECHNICAL FIELD

Subject matter disclosed herein relates generally to technologies for cardiac pacing and other therapies and, more particularly, to use of an elastic buffer implemented in hardware, which is also referred to as a hardware elastic buffer.

BACKGROUND

Implantable stimulation devices operate on limited power and limited memory. Storage of information relevant to the condition of a patient's heart consumes these precious resources. For example, a typical implantable stimulation relies heavily on software instructions to store information. Software consumes execution time and consequently shortens the longevity of the device. Accordingly, there is a need for improved information storage methods and devices that reduce software execution requirements.

SUMMARY

An exemplary implantable stimulation device includes a hardware elastic buffer. The implantable stimulation device is programmed to transmit information to and/or to retrieve information from the hardware elastic buffer. The implantable stimulation device optionally acquires information about a patient and transmits this information to a hardware elastic buffer for storage and/or subsequent retrieval.

The hardware elastic buffer optionally includes static random access memory (SRAM), or an equivalent thereof, and further optionally includes a buffer controller for routing information to SRAM and/or other memory. The buffer controller is also configurable to perform additional features, which include, without limitation, averaging, concatenating, and filling features.

In an exemplary implantable stimulation device, a buffer controller routes a piece of information to a first of a plurality of storage locations in a memory chip (e.g., a SRAM chip). Upon a request to store an additional piece of information, the information in the first storage location is shifted to a second storage location in the chip to make the first storage location available for the additional piece of information. Thus, in this elastic buffer, the buffer controller routes information to the first storage location.

In another exemplary implantable stimulation device, the device transmits an address to an elastic buffer. Next, the elastic buffer retrieves information from a data buffer based on the address. For example, the elastic buffer optionally includes a buffer controller having an address decoder for decoding the address wherein the decoded address corresponds to a storage location in the data buffer.

Overall, the hardware elastic buffers reduce computational requirements when compared to traditional implantable stimulation device buffers having similar features.

BRIEF DESCRIPTION OF THE DRAWINGS

Features and advantages of the described implementations can be more readily understood by reference to the following description taken in conjunction with the accompanying drawings.

FIG. 4 is a diagram of an exemplary arrangement for implementing a hardware elastic buffer.

DETAILED DESCRIPTION

Figure 1:
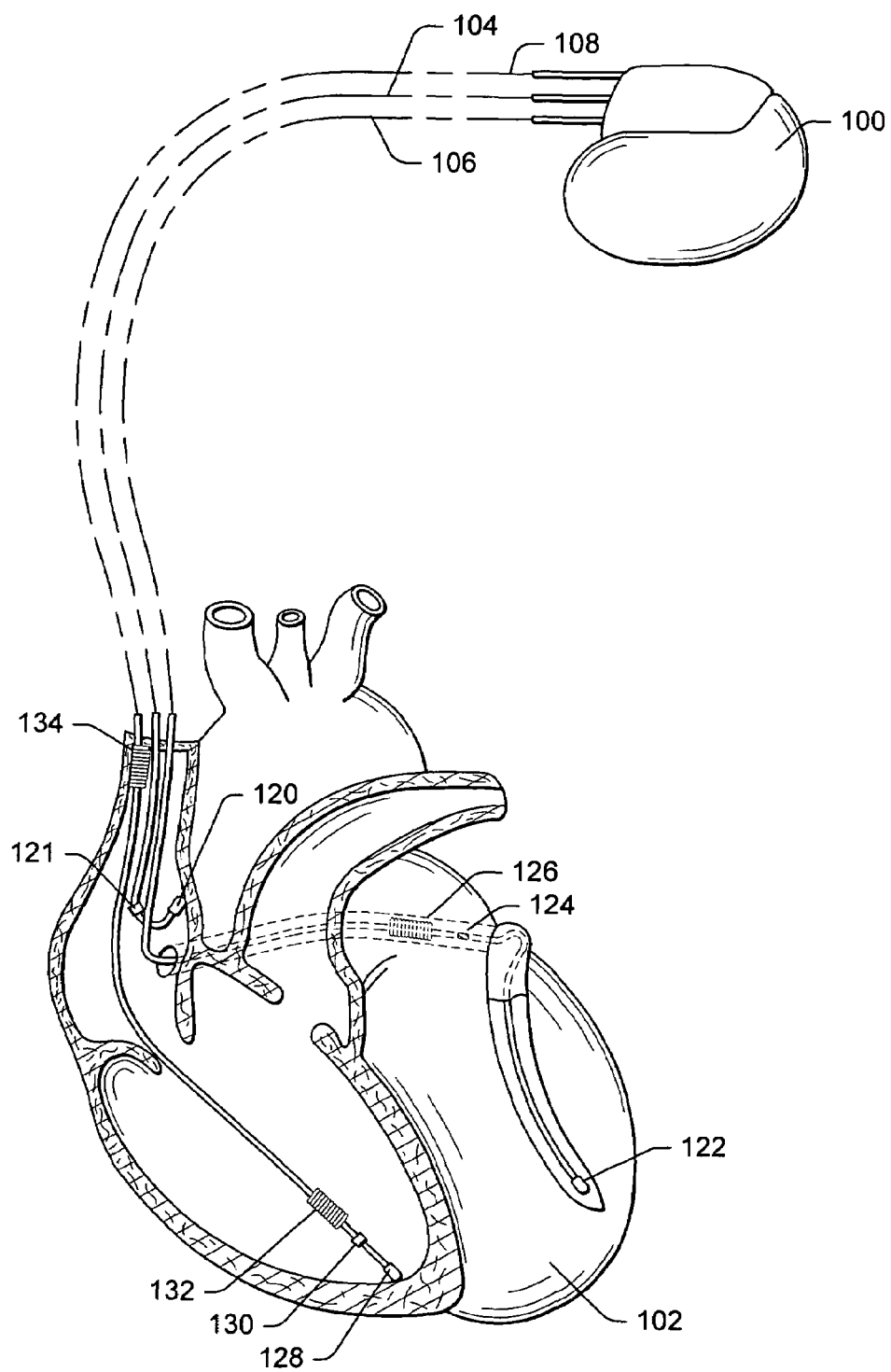
FIG. 1 is a simplified diagram illustrating an implantable stimulation device in electrical communication with at least three leads implanted into a patient's heart for delivering multi-chamber stimulation and shock therapy.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are generally used to reference like parts or elements throughout.

Overview

Implantable medical devices have finite memory and a finite supply of power. Further, memory usage places a heavy demand on the finite power supply. Thus, methods and devices that allocate memory efficiently are advantageous. As described herein, an implantable stimulation device benefits from the reduced computational requirements of an elastic buffer implemented in hardware.

An exemplary device includes an elastic buffer implemented in hardware that operates in a manner similar to a circular buffer. Circular buffers typically operate fully loaded and include a reallocation process that automatically eliminates data on a first-in-first-out (FIFO) basis. The location of the "old" deleted data is then used for storage of more recently acquired data, for example, newly acquired data or other buffered data. This reallocation process provides for a continual flow of resources for data storage and processing while typically reducing power demand.

In general, a circular buffer maintains separate read and write pointers to write data by one process and read data by another process. To prevent either overwriting of unread data or reading of invalid data, the buffer system prevents the read and the write pointers from passing each other. In an exemplary configuration of the present invention, a hardware-based elastic buffer requires only a single pointer. As described in more detail below, the present invention includes hardware-based elastic buffers where the term "elastic" refers generally to a buffer's flexibility. Further, the term "information" as used herein includes data.

A buffer implemented in hardware has several important advantages. For example, a hardware elastic buffer automatically generates and increments a pointer for memory accesses. This pointer wraps to the beginning of the buffer when its end is reached, thus saving the time and reducing the number of instructions otherwise needed to ensure that the address pointer stays within the boundary of the buffer. As a result, a hardware elastic buffer also speeds the execution of repetitive digital signal processing algorithms. In several exemplary systems described herein, hardware elastic buffers of the present invention take advantage of such features.

Exemplary Stimulation Device

The methods and devices described below are intended to be implemented in connection with any stimulation device that is, for example, configured or configurable to stimulate or shock a patient's heart.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
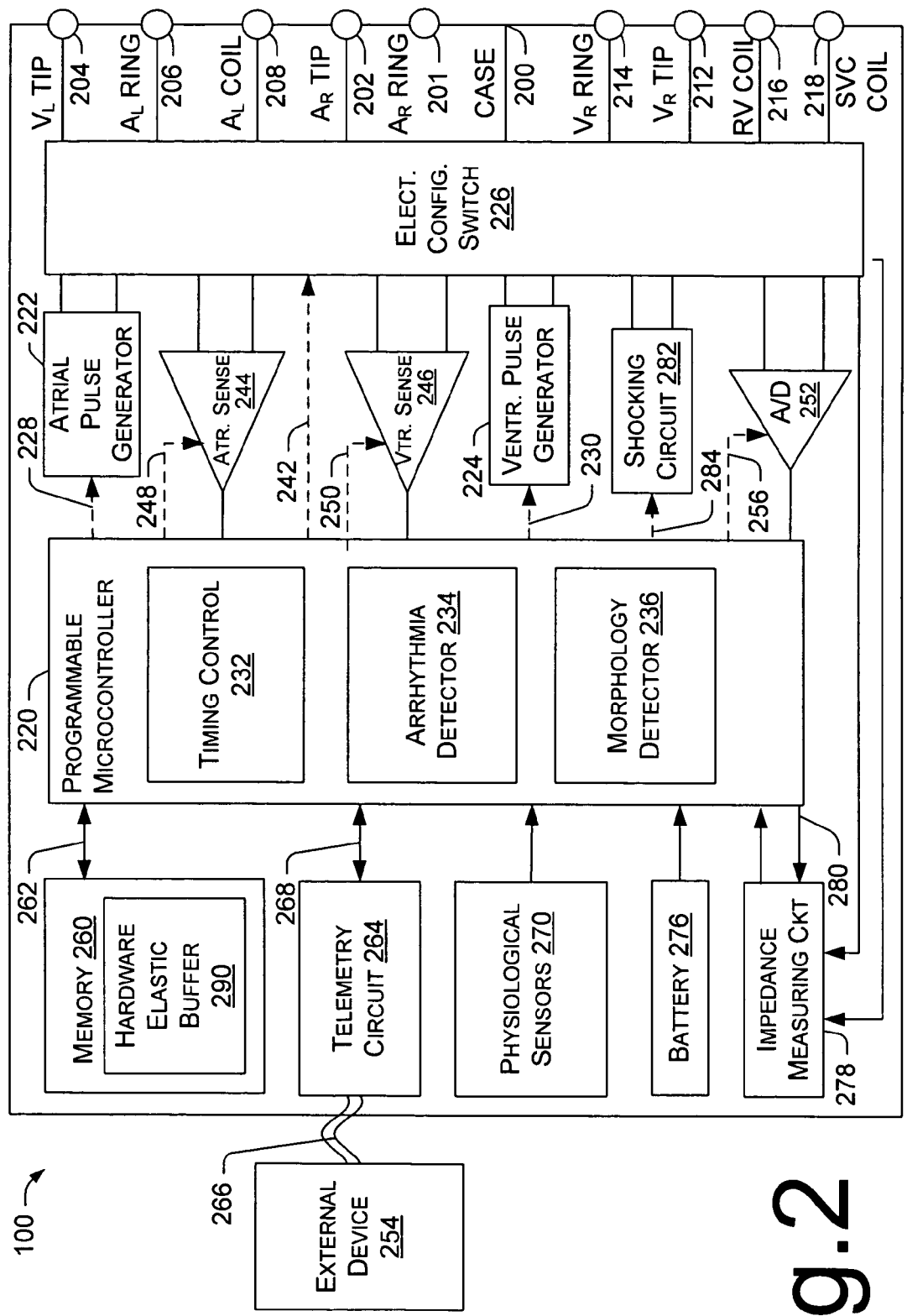
FIG. 2 is a functional block diagram of a multi-chamber implantable stimulation device illustrating basic elements that are configured to provide cardioversion, defibrillation, and pacing stimulation in four chambers of the heart.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the methods and devices described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120 (see also terminal ($A_R$ RING) 201). To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Sholder) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. The device 100 is optionally configured for bi-ventricular pacing therapy or cardiac resynchronization therapy (CRT).

Microcontroller 220 further includes an arrhythmia detector 234 and a morphology detector 236. These components can be utilized by the stimulation device 100 for determining desirable times to administer various therapies. The components 234 and 236 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

The microcontroller 220 is further coupled to a memory 260 by a suitable data/address bus 262, wherein programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

As shown in FIG. 2, the memory 260 includes a hardware elastic buffer 290. The hardware elastic buffer 290 is described in more detail below. Further, devices suitable for use as memory (e.g., 260, 290) and methods of operating and using memory (e.g., 260, 290) are described in detail below.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include physiological sensors 270, such as a physiologic sensor commonly referred to as a "rate-responsive" sensor because it is typically used to adjust pacing stimulation rate according to the exercise state of the patient. However, the physiological sensors 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiological sensors 270 may also be external to the stimulation device 100, yet still be implanted within or carried by the patient. Examples of physiological sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state.

The physiological sensors 270 optionally include sensors for detecting movement and minute ventilation in the patient. Any sensor capable of sensing changes in movement or minute ventilation, either directly or indirectly may be used. The physiological sensors 270 further optionally include a minute ventilation (MV) sensor to sense minute ventilation, which is defined as the total volume of air that moves in and out of a patient's lungs in a minute.

The stimulation device 100 may also be equipped with a GMR (giant magnetoresistance) sensor and circuitry 275 that detects the earth's magnetic fields. The GMR sensor and circuitry 275 may be used to ascertain absolute orientation coordinates based on the earth's magnetic fields. The device is thus able to discern a true vertical direction regardless of the patient's position (i.e., whether the patient is lying down or standing up).

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium derivative battery chemistries.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of, for example, low (up to 0.5 Joules), moderate (0.5 to 10 Joules), or high energy (11 to 40 Joules), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level and pertaining to the treatment of fibrillation. Accordingly, the microcontroller 220 is capable of controlling the synchronous or asynchronous delivery of the shocking pulses.

Hardware Elastic Buffer

Figure 3:
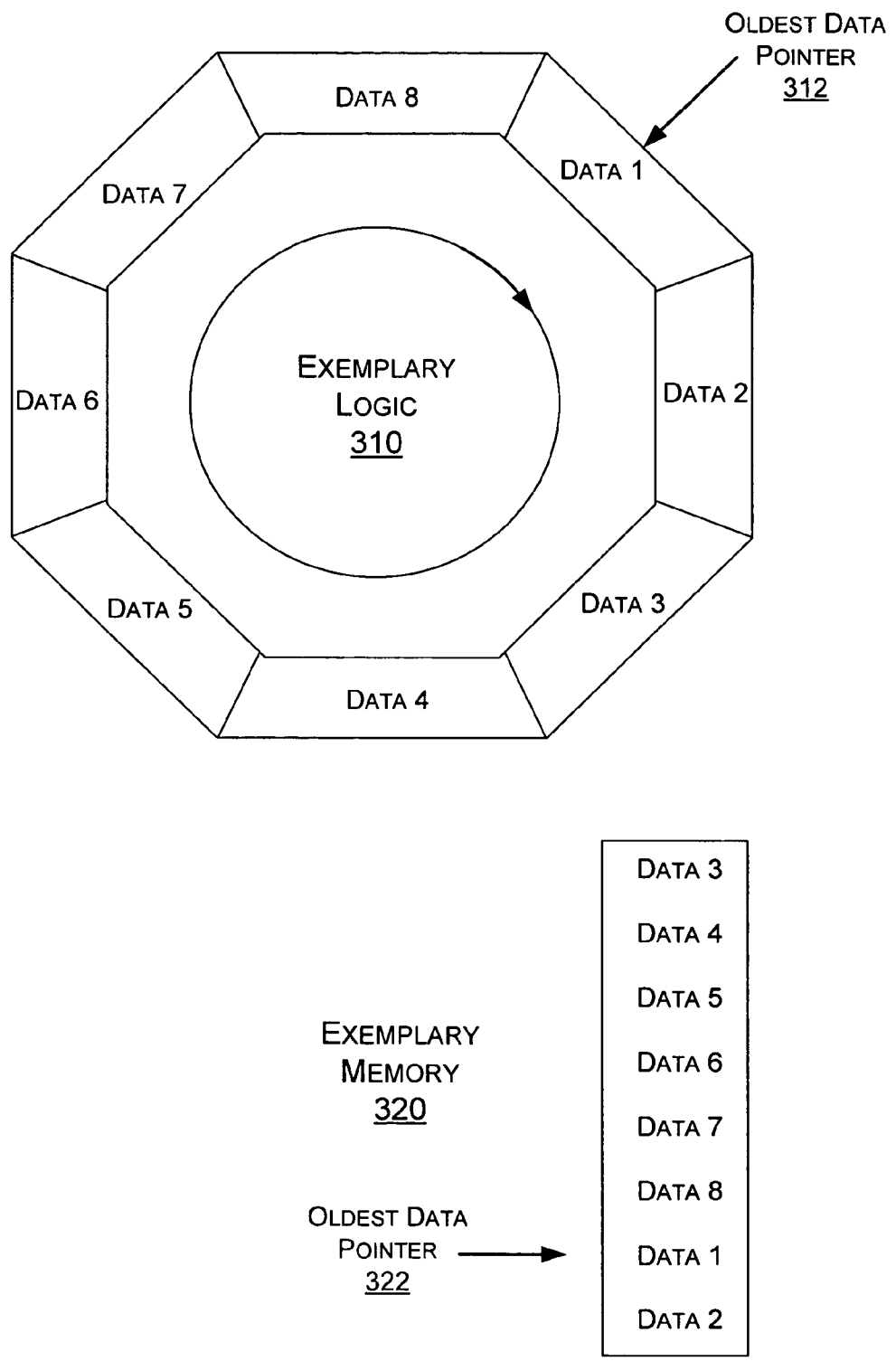
FIG. 3 is a diagram of an exemplary logic schematic and a corresponding exemplary memory schematic for a hardware elastic buffer.

FIG. 3 shows an exemplary logic schematic 310 and a corresponding exemplary memory schematic 320 for a hardware elastic buffer. The logic schematic 310 illustrates a circular buffer where data is written to the eight data buffers in a clockwise manner. An oldest data pointer 312 points to the oldest data in the circular buffer (e.g., Data 1). As data is successively written to the buffer, the oldest data pointer 312 will track the oldest data in the buffer. Thus, the data pointer 312 will increment from Data 1 to Data 2 when Data 1 is overwritten and from Data 2 to Data 3 when Data 2 is overwritten until the pointer 312 reaches Data 8 where it will return to Data 1 when Data 8 is overwritten.

The exemplary memory schematic 320 illustrates a linear representation of data in memory. An oldest data pointer 322 points to the oldest data in the memory. As data is successively written to the memory, the oldest data pointer 322 will track the oldest data in the memory. However, tracking must account for the linear representation of data in the memory. As described herein an exemplary elastic buffer provides for tracking in a circular yet elastic manner.

FIG. 4 shows an exemplary arrangement 400 for implementing a hardware elastic buffer. The exemplary arrangement 400 includes data 410 for various times (Time 1, Time 2, Time 3) that correspond to stored data 420 for the various times (Time 1, Time 2, Time 3) wherein exemplary logic 430 allows for an association between the data 410 and the stored data 420. In this example, the data 410 represent data read from memory, i.e., the stored data 420.

The data 410 includes Data 1 at Time 1, Data 2 at Time 2 and Data N at time N ordered by entry order; whereas, the stored data 420 includes data ordered by address. As mentioned with respect to FIG. 3, an oldest data pointer points to the oldest data, which is initially "Data 1". In the example of FIG. 4, exemplary logic 430 provides a pointer that points initially to an address for Data 1 and after each successive entry of data to the data store (e.g., memory), the pointer is incremented until it points to the address of Data N. Then, upon the next entry, the pointer circles back to the address for Data 1. The exemplary logic 430 is elastic in that "N" may be selected and it allows for "circular" behavior in that the pointer can circle back to an initial address.

An exemplary scenario provides for writing data using such exemplary logic by first writing data to an insert data register. A read command causes a read of the pointer, which returns an address for the oldest data. The logic then calls for writing the data in the insert data register to the pointer address, which overwrites the oldest data. The logic also calls for incrementing the pointer such that the pointer continues to point to the address for the oldest data.

Another exemplary scenario provides for reading the register for the newest data. In this scenario, a read command causes a read of the pointer, which returns an address for the oldest data. The logic then adds the size of the buffer (e.g., "N"), divides by the size of the buffer and uses the remainder as the address and returns the data at the specified address.

In yet another exemplary scenario, a read command reads a register for the oldest data element which causes a read of the pointer which returns an address for the oldest data. The data is then provided using the address.

Figure 5:
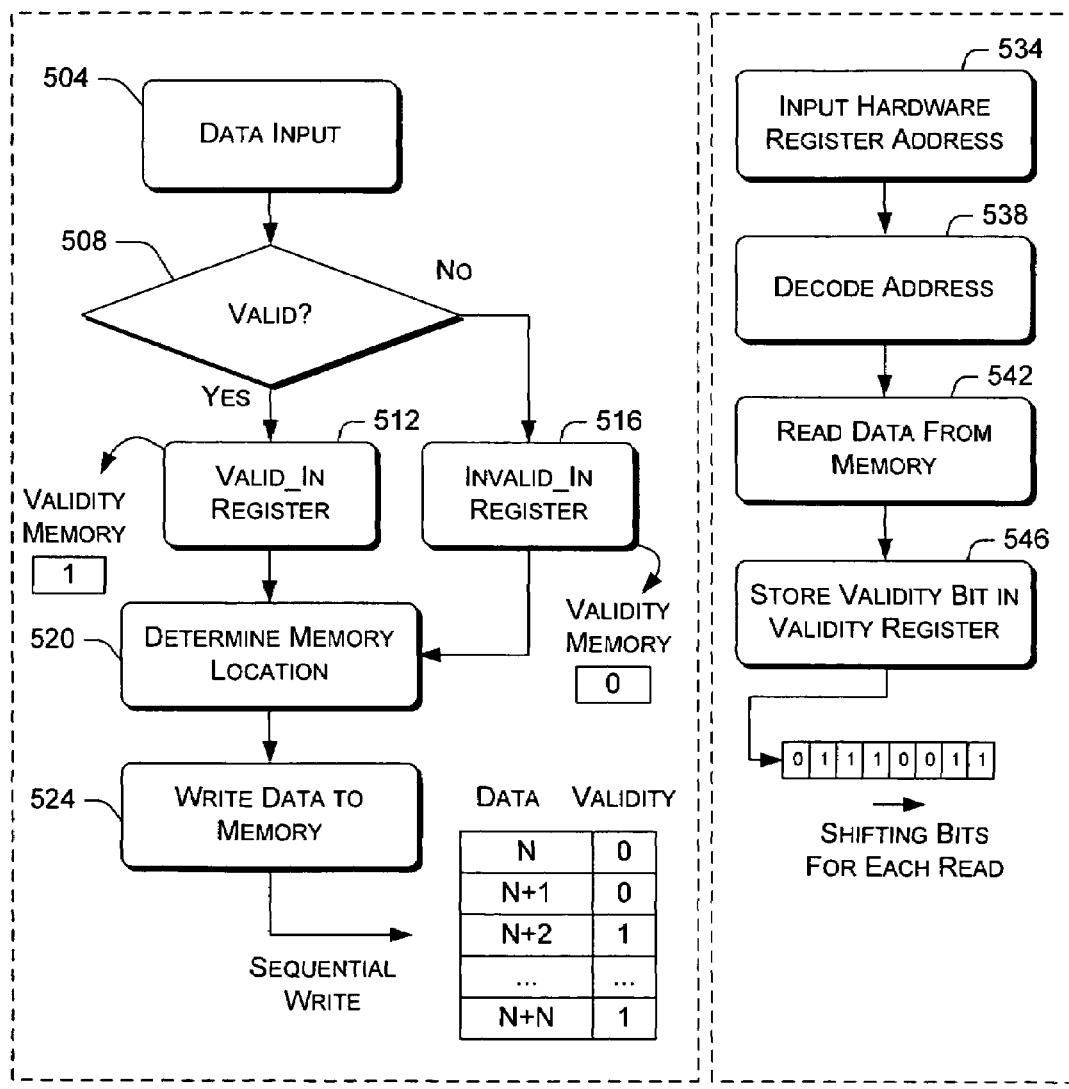
FIG. 5 is a functional block diagram of exemplary methods for writing data to memory and reading data from memory.

FIG. 5 shows an exemplary method 500 that includes a method 510 for writing data to memory and a method 530 for reading data from memory where both methods include use of a validity indicator. The exemplary method 510 includes a data input block 504 for inputting data. A decision block 508 follows that decides whether the data is valid or invalid. If the decision block 508 decides that the data is valid, then the data is placed in a valid register 512 (e.g., Valid_In); whereas, if the data is invalid, then the data is placed in an invalid register 516 (e.g., Invalid_In). In conjunction with the decision of the decision block 508, a validity memory is used, for example, to store a "1" to indicate validity of the data or to store a "0" to indicate invalidity of the data.

Regardless of the decision, a determination block 520 follows that determines a memory location for the data. The location is used by a write block 524 that writes the data to memory. In the example shown, data and validity information are stored in an associated manner. In various examples discussed herein the data memory is referred to as a data buffer and the validity memory is referred to as a validity buffer.

An exemplary method thus writes data to either a valid register or an invalid register and then relies on exemplary logic to determine an appropriate memory location in which to store the data. In this example, the exemplary logic receives hardware register addresses and correlates these addresses to relative memory addresses. In an implementation that uses SRAM, an address decoder and a pointer operate according to such logic. For example, an exemplary SRAM controller includes an address decoder and a pointer that operate in conjunction with SRAM to according to the aforementioned logic.

The exemplary method for reading data from memory 530 commences with an input block 534 that receives a hardware register address. A decoder block 538 decodes the hardware register address to provide a memory address. A read block follows 542 that uses the memory address to read data from memory. As already mentioned, the data may be associated with validity information; thus, the read may retrieve validity information. In the exemplary method 530, the validity information is in the form of a bit, which is read and, per a storage block 546, is stored in a validity register. The validity register may have a particular length and operate by shifting bits within the register as new validity bits are stored to the register. The data read from the memory may be stored in an appropriate data register (not shown) or otherwise communicate via a bus, etc.

Figure 6:
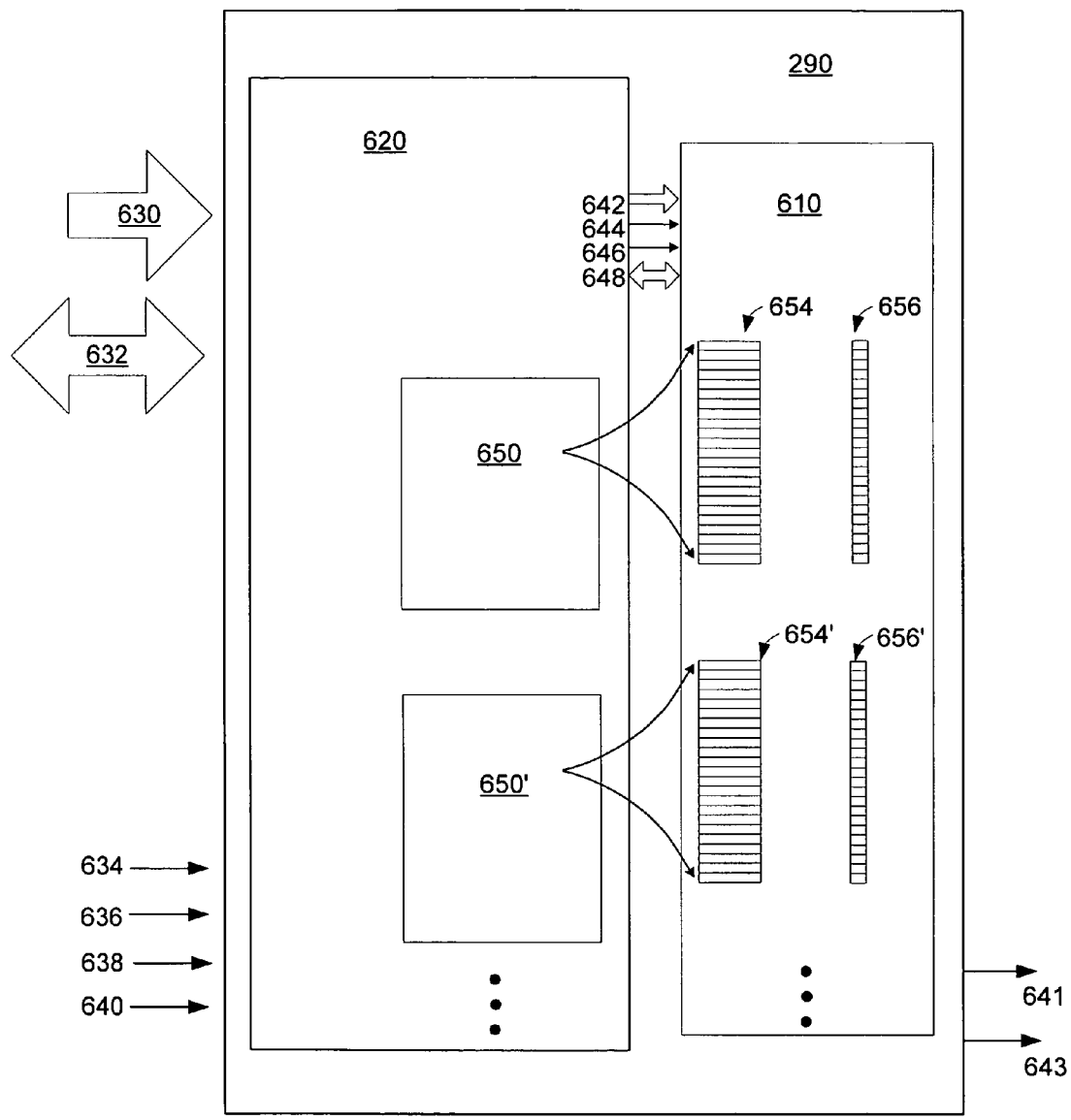
FIG. 6 is a functional block diagram of a hardware elastic buffer suitable for use with the implantable stimulation device described in FIGS. 1 and 2. This hardware elastic buffer diagram illustrates basic elements that are configured to route information to and/or from memory.

FIG. 6 shows an exemplary hardware elastic buffer 290 for storing information, such as data related to cardiac condition. The elastic buffers and corresponding methods disclosed herein can be implemented in connection with any suitably configured stimulation device. One specific and non-limiting example of a stimulation device was described above with respect to FIGS. 1 and 2.

In several of the diagrams presented herein, various algorithmic acts are summarized in individual "blocks". Such blocks describe specific actions or decisions that are made or carried out as a method of process proceeds. Where a microcontroller (or equivalent) is employed, the diagrams presented herein provide a basis for a "control program" or software/firmware that may be used by such a microcontroller (or equivalent) to effectuate the desired control of the stimulation device. As such, the methods of operating, for example, the systems shown in FIGS. 1 and 2, are implementable as machine-readable instructions stored in memory that, when executed by a processor, perform various acts illustrated as blocks or otherwise.

Those skilled in the art may readily write such a control program based on the diagrams and other descriptions presented herein. It is to be understood and appreciated that the subject matter described herein includes not only stimulation devices when programmed to perform operations described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

The exemplary hardware elastic buffer accepts information through at least one input and outputs information through at least one output. An input and output optionally operate over a single bi-directional bus or receiver/emitter. The exemplary elastic buffer 290 includes static random access memory (SRAM) 610 and a SRAM controller 620 for controlling information exchange with the SRAM 610. In general, SRAM does not need to be refreshed like dynamic random access memory (DRAM) and has shorter access times than DRAM.

In addition to the SRAM 610 and SRAM controller 620, the elastic buffer 290 has a variety of inputs and outputs to exchange information with devices external to the elastic buffer 290, including, for example, an address bus 630, a bi-directional data bus 632, an active low elastic buffer sub-block select logic signal input 634, an elastic buffer system logic clock signal input 636, a read/write logic signal input 638, an active low system master hardware reset logic signal input 640, a clock request logic signal output 641 and a elastic buffer select feedback logic signal output 643.

Through use of these various information inputs and/or outputs, or others, the SRAM controller 620 routes information to and/or from a plurality of integral elastic buffer sub-blocks 650, 650', etc. The elastic buffer sub-blocks 650, 650', etc. are optionally divided into groups of 2, 4, 8, etc. For example, a system having a total of 16 sub-blocks arranged as two individual 8-sub-block blocks may be used.

To store information, each sub-block 650 has corresponding SRAM, represented by a 32-byte SRAM data buffer 654, 654', etc. The SRAM data buffers 654 have first-in-first-out (FIFO) functionality wherein the first data written to the data buffer 654 is the first data out of the data buffer; however, in addition to FIFO functionality, the elastic buffer 290 can access any of the 32 bytes within each data buffer 654 at any time in any order.

The elastic buffer 290 shown in FIG. 3 also features a plurality of SRAM validity buffers 656, 656', etc. for storing the valid or invalid status of each data byte within corresponding data buffers 654, 654', etc. With the addition of validity buffers 656, the SRAM controller 620 has the ability to track data validity. For example, the SRAM controller 620 can write data to one of two SRAM "data in" registers, one corresponding to valid data and the other corresponding to invalid data. When the SRAM controller 620 routes the data from one of the data registers to a data buffer 654, the validity status can be recorded in a corresponding validity buffer 656. Thus, through use of the validity buffers 656, the system 690 has the ability to track the validity status of all data within the SRAM data buffers 654.

According to the elastic buffer 290 shown in FIG. 6, the SRAM controller 620 transfers information to and/or from the SRAM using a SRAM address bus 642, a SRAM control signal 644, a SRAM read/write logic signal input 646, and a bi-directional SRAM data bus 648, which transfers data and/or other information, such as, validity information.

Overall, the elastic buffer 290 functions in a circular manner, like a circular buffer. For example, as the elastic buffer 290 writes new data bytes into one of the data buffers 654, all data bytes, presently stored in that data buffer 654, shift to a neighboring byte address with the exception of the last byte, which the elastic buffer may purge or simply overwrite. Of course, the elastic buffer may shift and, if required, purge or overwrite corresponding validity bits stored in the corresponding validity buffer 656 to maintain the proper validity status of each of data buffer byte. Alternatively, in an exemplary elastic buffer, a concatenation feature shifts the last byte to another data buffer, e.g., 654'.

In addition to the features described thus far, each elastic buffer sub-block 650, in conjunction with the SRAM controller 620, has the ability to calculate and/or store a moving average that changes in response to recently added buffer data. The elastic buffer 290 controls this averaging feature by setting the number of data bytes to be averaged. Accordingly, the elastic buffer 290 optionally selects averaging of, e.g., 4, 8, or 16 of the most recent data bytes or it simply disables the feature. Of course, the averaging feature may optionally incorporate techniques for calculating weighted averages as well as other techniques known to one of ordinary skill in the art of control systems (forgetting factors, etc). Various averaging features are described in more detail below (see, e.g., Averaging Feature). Another feature allows the elastic buffer 290 to clear all bytes in each data buffer 654, 654', etc., and/or to set all bytes in each data buffer 654, 654', etc., to a particular value using a fill function.

Figure 7:
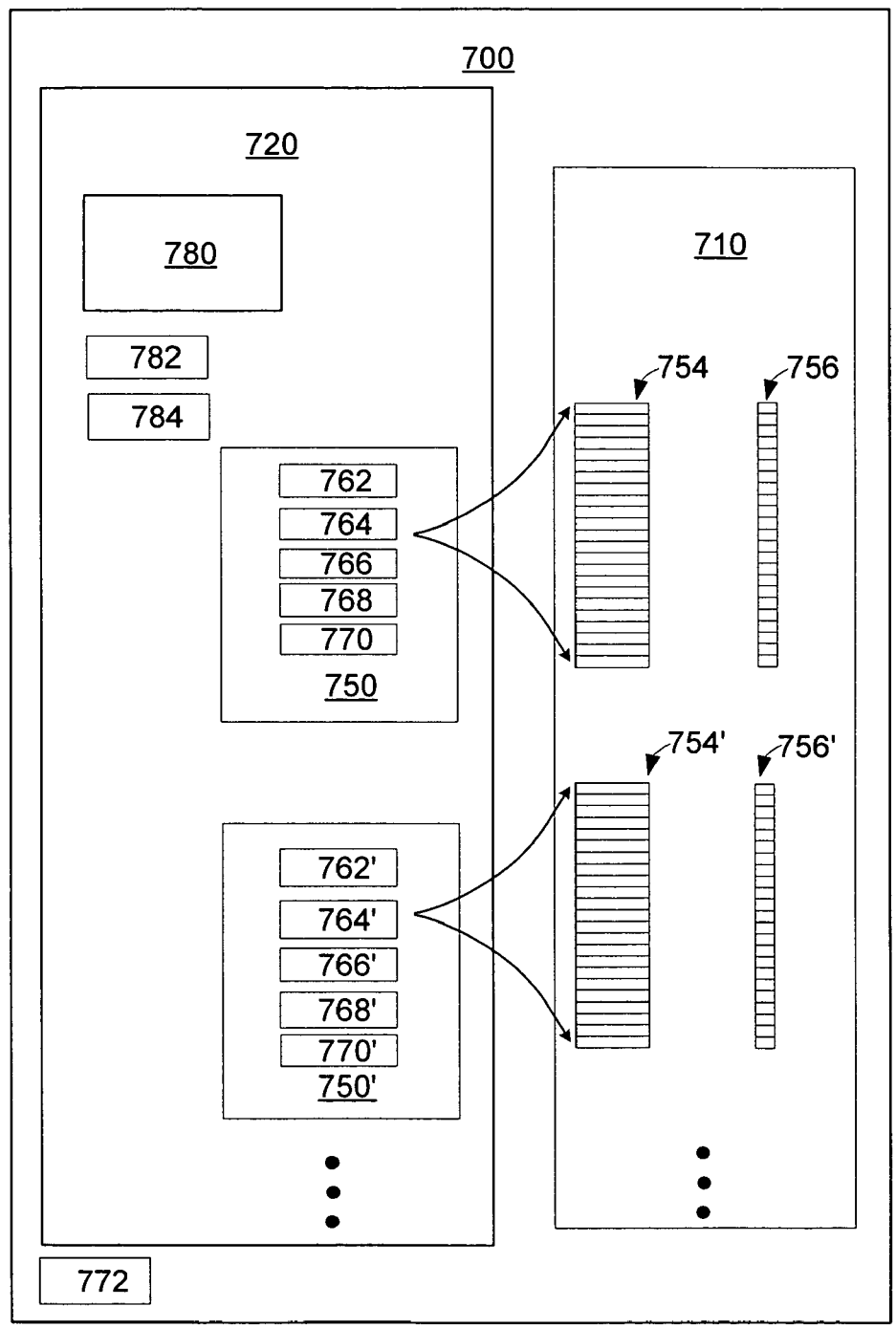
FIG. 7 is a functional block diagram of a hardware elastic buffer corresponding generally to the hardware elastic buffer shown in FIG. 6. The hardware elastic buffer shown in FIG. 7 is suitable for use with the implantable stimulation device described in FIGS. 1 and 2. The diagram shown illustrates basic elements that are configurable and/or useful to enable certain operational features.

FIG. 7 shows a more detailed exemplary elastic buffer 700 having the capabilities of the elastic buffer 290 shown in FIG. 6. Referring to FIG. 7, the elastic buffer 700 routes data to and/or from SRAM 710 using a SRAM controller 720. The SRAM controller 720 manages information read from and written to SRAM 710, which includes, for example, two 256×9 bit SRAM chips.

As shown in FIG. 7, the sixteen 32 byte SRAM data buffer blocks (754, 754', etc.) of the two 256×9 bit SRAM chips associate with sixteen elastic buffer sub-blocks (750, 750', etc.). In addition, each of the elastic buffer sub-blocks 750 has five hardware registers: a configuration register 762, a valid register 764, an invalid register 766, a validity register 768 and one average register 770. The average register 770 contains an average of specified elastic buffer data according to the averaging configuration (e.g., as specified in the configuration register 762). Regarding data averaging, the average register 770 operates in conjunction with the SRAM controller's average calculate register 782 and average hold register 784 (described in more detail below). The SRAM controller 720 manages the transfer of data to and from the hardware registers of each elastic buffer sub-block 750 to the associated SRAM 710 through use of an address decoder 780.

The address decoder 780 works to vector hardware addresses to relative SRAM addresses. In this exemplary elastic buffer 700, only hardware register addresses must be specified by firmware/software to read and write data to SRAM 710. The address decoder 780 determines the appropriate SRAM storage location in which to place data that has been written to either an elastic buffer sub-block's valid register 764 or invalid register 766.

The SRAM controller 720 writes data to sequential address locations in the SRAM 710 using the address decoder 780 and a pointer. Once 32 bytes of data have been written to a particular SRAM data buffer 754, the newest data byte will replace (e.g., write over) the oldest data byte. Upon reaching the last address of that data buffer 754, the pointer moves back to that buffer's first available address space and subsequently writes over the existing data in that location upon receipt of new data.

In this system 700, hardware keeps track of the SRAM address of the most recent data write. Unique pointers for each data buffer 754 monitor the location of the most recent addition to that data buffer 754. For example, the first hardware address of an elastic buffer sub-block's 750 corresponding data buffer 454 indicates the most recent data byte and the 32nd hardware address of indicates the oldest addition to that elastic buffer sub-block 750.

When reading data, the address decoder 780 uses the pointer to determine the most recent addition to a particular data buffer 754 and decode this memory location to the starting address of the buffer range. In this manner, a read to the starting address of the data buffer 754 will result in a read of the most recent data.

Configuration Register

For further utility, the SRAM controller 720 includes additional programmable features. For example, several user programmable features involve use of the configuration register 762 of an elastic buffer sub-block 750. Accordingly, the particular configuration stored in a sub-block configuration register 762 determines how to route data to the associated buffers. For example, a configuration register entry can indicate whether to buffer fill, to concatenate, or to use 4, 8, or 16 data bytes in an average. When used, the configuration register 762 should be set prior to the first write to the valid register 764 and/or invalid register 766 (and subsequently the SRAM data buffer 754) of that elastic buffer sub-block 750. If not set, the configuration register 762 contains a default value.

In an exemplary elastic buffer, once configured for averaging, the SRAM controller commences averaging on the next data write to the elastic buffer sub-block 750. In an elastic buffer configured for fill, the fill feature takes precedence to any other feature that can be turned on. For example, if both the fill feature and "average as data in" feature are configured simultaneously, the fill feature will commence followed by the "average as data in" feature. Thus, after the fill operation is complete, the average as data in feature commences on the next operation associated with the particular elastic buffer sub-block 750. Regarding concatenation, this feature normally takes priority over the "average as data in" feature. For example, if an elastic buffer sub-block 750 is configured as both a concatenated buffer and as "average as data in", the buffer will concatenate with the previous buffer and the "average as data in" feature will be ignored. In general, the combination of concatenation and "average as data in" features is seldom desirable and often avoided.

Validity and Invalidity Registers

As already mentioned, information generally enters a SRAM data buffer through either the valid register 764 or the invalid register 766 of the corresponding elastic buffer sub-block 750. For example, when a valid data byte enters the SRAM controller 720, the elastic buffer 700 stores the valid data byte in the valid register 764 whereas, when an invalid data byte enters, the elastic buffer stores the invalid data byte in the invalid register 766. In one mode of operation, the SRAM controller 720 writes a "one" or a "zero" to a corresponding SRAM validity buffer 756 to indicate whether data destined for the data buffer 754 was written to a valid register 764 or an invalid register 766. Accordingly, each time the elastic buffer 700 writes a new data byte to a valid register 764 or an invalid register 766, the SRAM controller 720 updates the corresponding SRAM validity buffer 756. In alternative modes of operation, the SRAM validity buffer 756 bit indicates a generic classification of the data or operates as a 9th bit for 9-bit data. Of course, a SRAM "validity buffer" having more than a one-bit depth is within the scope of the present invention and useful for implementing a variety of features.

In an exemplary elastic buffer shown in FIG. 7, the validity buffer 756 stores information indicative of some data characteristic, typically the valid/invalid status of each data byte. In one mode of operation, the SRAM controller 720 inputs each of 32 validity bits to the SRAM 710 as the most significant bit. As such, this bit accompanies the byte data sent to the SRAM 710 and indicates whether or not the byte data is valid. For example, when the elastic buffer 700 writes to the valid register 764, the SRAM controller 720 sets the first bit in the validity buffer 756 to 1, whereas, when the elastic buffer 700 writes to the invalid register 766, the SRAM controller sets the first bit in the validity buffer 756 to 0.

Regarding the sequence of events for the elastic buffer 700 shown in FIG. 7, note that upon a write to a data buffer, the elastic buffer requests a "first cycle" elastic buffer clock check; thus, the actual write to the SRAM 710 occurs subsequently, e.g., on the second cycle. This particular first cycle-second cycle sequence applies for a write to a non-concatenated buffer only because a write to a concatenated buffer requires more cycles. In general, a write to a valid register 764 or an invalid register 766 automatically updates both the SRAM data buffer 754 and the SRAM validity buffer 756. Also note that, according to the elastic buffer 700 shown in FIG. 7, upon a request for a write and subsequent SRAM 710 selection, a SRAM data bus connects to a hardware data bus. Once the address decoder 780 decodes the hardware address, the SRAM controller 720 places the appropriate data on the SRAM data bus and sends the information to the SRAM 710.

As mentioned previously, each elastic buffer sub-block 750 includes a validity register 768. The SRAM controller 720 stores a validity bit, from a validity buffer 756, in the validity register 468 each time the controller 720 reads a byte from the SRAM 710. In general, the SRAM controller 720 inputs validity bits sequentially into the appropriate validity register 468, locating the most recent addition to the register 768 at the location of the most significant bit (MSB). Thus, each time the SRAM controller 720 reads a new data byte, the validity bits are shifted in the appropriate validity register 768. In the elastic buffer 700 of FIG. 7, after 8 bytes of data have been read, the SRAM controller 720 purges or overwrites the oldest validity bit as a new validity bit is written to the MSB location of the corresponding validity register 768.

Busy Register

The elastic buffer 700 shown in FIG. 7 also includes a busy register 772. The busy register 772 indicates when the elastic buffer 700 is "busy" completing internal tasks (e.g., hardware functions). To perform this function adequately, an implantable stimulation device has the ability to read the busy register 772 and the elastic buffer has the ability to make available the contents of the busy register 772 at any time. When set to "busy", the elastic buffer does not accept writes to the elastic buffer sub-blocks 750. During "busy", reads to the hardware registers result in valid data; however, the elastic buffer 700 prohibits reads to any of the elastic buffer SRAM data buffers 754 (which optionally return a default value upon occurrence of a "prohibited" read).

Concatenation Feature

An elastic buffer optionally implements a concatenation process. Elastic buffers 290 and 700 optionally allow each elastic buffer sub-block to concatenate its data buffer with a previous block's data buffer. For example, the elastic buffer 700 of FIG. 7 controls the concatenation feature through use of a configuration register 762 wherein assigning a "zero" or a "one" to a particular bit either turns off or turns on the concatenation feature.

In an example, two elastic buffer sub-blocks and their corresponding data buffers and validity buffers are used where the elastic buffer sub-blocks have corresponding configuration registers, valid registers and invalid registers. When enabled, the concatenation feature instructs the SRAM controller to write the "oldest" data byte of the preceding data buffer to either the valid register or invalid register (depending on validity) of the subsequent elastic buffer sub-block. The SRAM controller also places the "newest" data byte in the data buffer from which the "oldest" data byte was transferred. The controller also transfers the "oldest" bit in the validity buffer to the subsequent validity buffer to prevent losing the relationship between the transferred data byte and its validity status.

Figure 8:
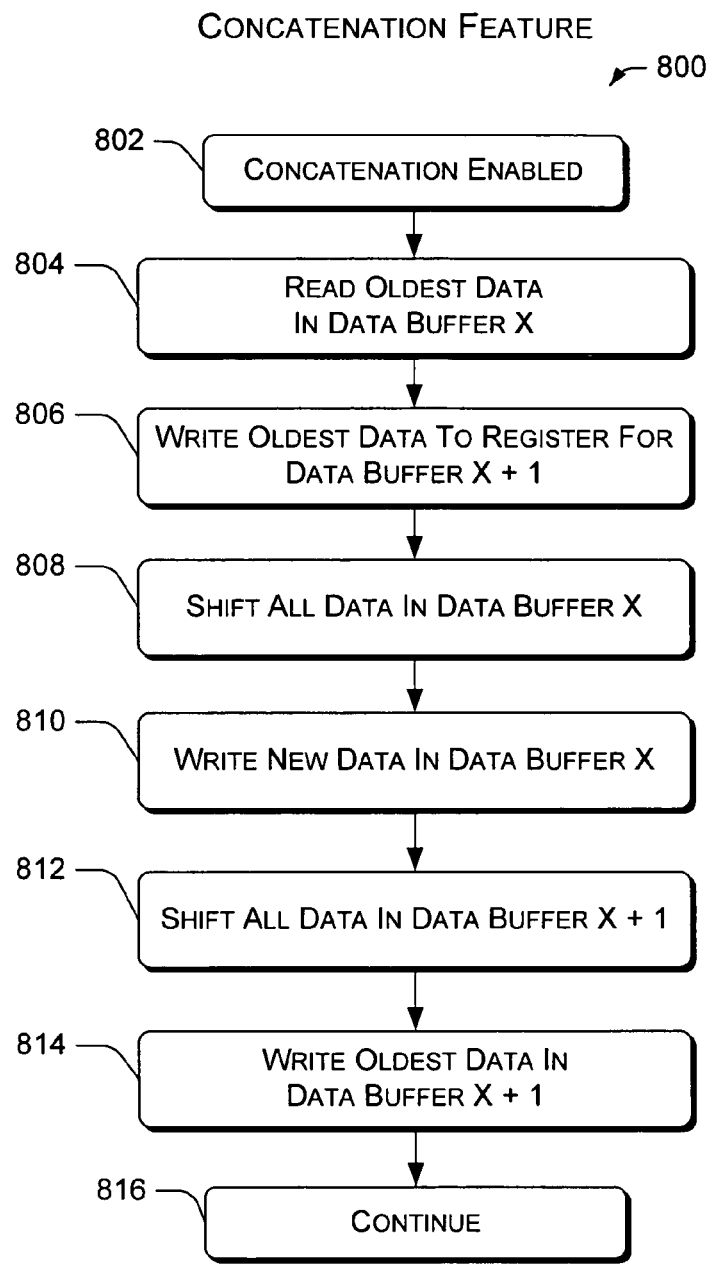
FIG. 8 is a functional block diagram of a concatenation feature for use in an implantable stimulation device.

A concatenation method 800 is illustrated in FIG. 8. A concatenation block 802 checks to determine whether concatenation is enabled. If concatenation is enabled, then a read block 804 reads the oldest data in data buffer X, wherein X corresponds to any data buffer except the last data buffer. Next, a write block 806 writes the oldest data to a data in register for data buffer X+1. A shift block 808 then shifts all data in data buffer X, which consequently deletes the oldest data from data buffer X. Next, a write block 810 writes new data to data buffer X. A similar procedure occurs for data buffer X+1 wherein a shift block 812 shifts all data in data buffer X+1 and a write block 814 writes the oldest data from the data in register to data buffer X+1. This process continues (continuation block 816) accordingly as new data enters the hardware elastic buffer.

In instances where the elastic buffer sub-blocks are arranged in groups, concatenation generally occurs within groups. For example, in an elastic buffer with 16 elastic buffer sub-blocks in two groups, sub-blocks in one group can be concatenated with each other and sub-blocks in the other group can be concatenated with each other, but sub-block data from the first group cannot be concatenated with a sub-block from the second group. In addition, while possible, concatenation generally does not occur between a group's first sub-block and last sub-block.

Averaging Feature

As already mentioned, the present invention optionally includes an averaging feature. For example, consider the elastic buffer 700 shown in FIG. 7, wherein the SRAM controller 720 has an average calculate register 782 and an average hold register 784 and each elastic buffer sub-block 750 has an average register 770. In such an elastic buffer, a bit, or bits, in each elastic buffer sub-block 750 configuration register 762 determine how the average calculate register 782 and average hold register 784 interact with data from the corresponding data buffer 754.

According to one exemplary elastic buffer, a SRAM controller sets bits in a configuration register to control the averaging feature. In this elastic buffer, bits in the configuration register determine the on/off status of the averaging feature and the number of data bytes averaged by the averaging feature. For example, the elastic buffer 700 shown in FIG. 7 has a configuration register 762 wherein two bits determine whether the averaging feature averages 4, 8 or 16 data bytes. The averaging feature typically updates the average upon acquisition of each new data byte.

Regarding the sequence of events related to an averaging feature, such as that of the elastic buffer 700 shown in FIG. 7, certain events, which typically occur in some determinable amount of time, must execute to properly calculate an average. The number of events and hence, the amount of time, varies according to the number of data bytes averaged. Referring again to the elastic buffer 700 of FIG. 7, the SRAM controller 720 sets the busy register 772 to "busy" during execution of certain averaging related events.

In an exemplary averaging process, with reference to the elastic buffer 700 of FIG. 7, a SRAM controller 720 reads the specified number of data bytes from a SRAM data buffer 754. Each of these data bytes then enters the SRAM controller's average calculate register 782, which sums each data byte with previously read data bytes up to the pre-determined number of data bytes. Once the SRAM controller 720 enters the pre-determined number of data bytes in the average calculate register 782, a division step occurs that divides the sum by the pre-determined number of data bytes to produce the average. Next the SRAM controller 720 places the average in the average hold register 784. Subsequently, the SRAM controller 720 places the average in the average register 770 of the corresponding elastic buffer sub-block 750.

Figure 9:
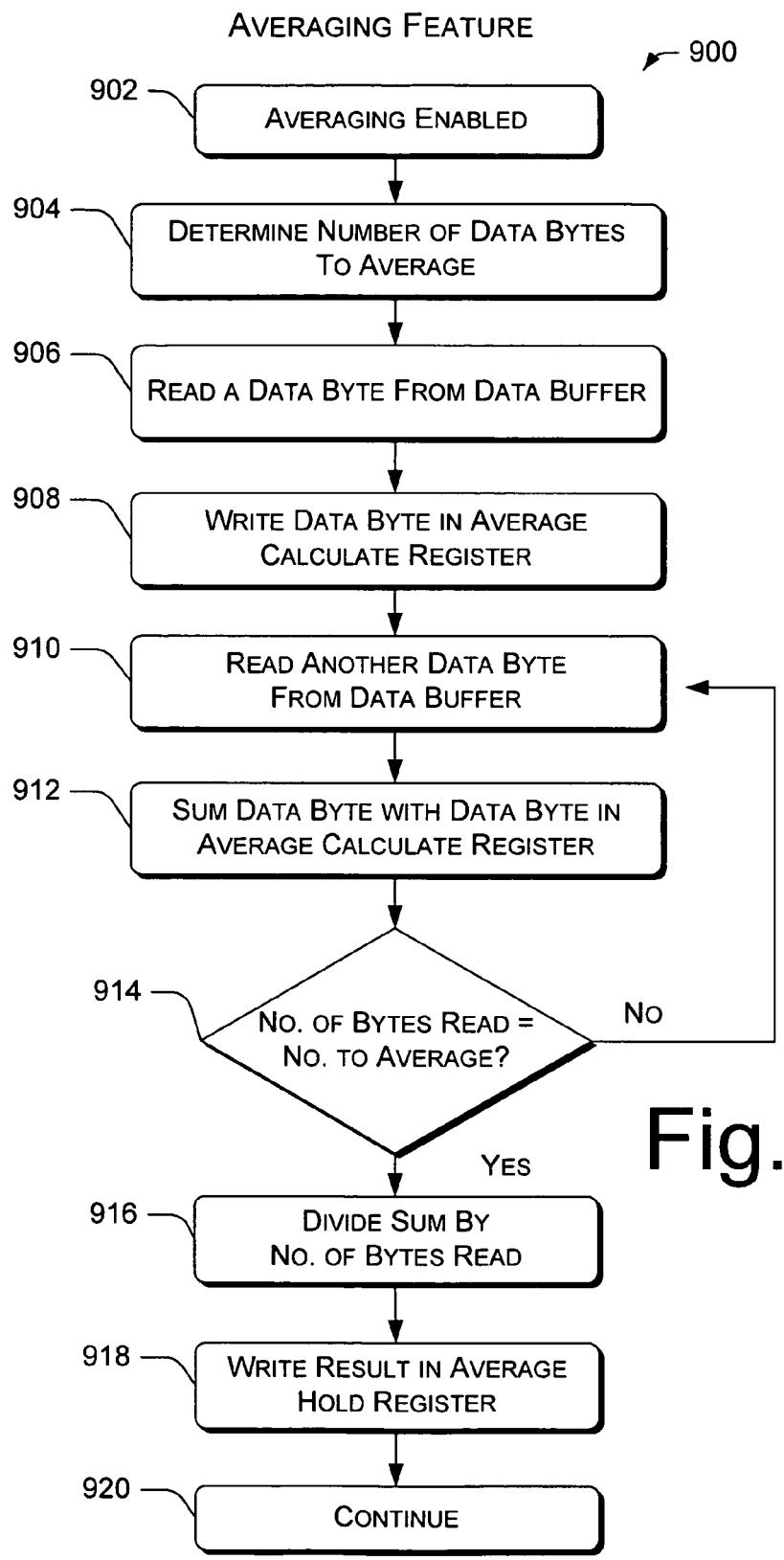
FIG. 9 is a functional block diagram of an averaging feature for use in an implantable stimulation device.

FIG. 9 shows a flow chart of this averaging method 900. An averaging block 902 checks to see if averaging is enabled within the particular elastic buffer sub-block, e.g., by checking the configuration of the configuration register. If averaging is enabled, then the information contained in the configuration register also contains the number of data bytes to average and a determination block 904 determines that number for purposes of the averaging method 900. Next, a read block 906 reads a data byte from a data buffer corresponding to the elastic buffer sub-block. A write block 908 then writes this data byte to the average calculate register of the elastic buffer controller. After this first byte has been written to the average calculate register, another read block 910 reads another data byte from the data buffer. A sum block 912 then sums this data byte with the data byte already in the average calculate register. A check block 914 follows which checks if the appropriate number of data bytes have been read, written and summed. If the number is less than that specified, the read 910, sum 912 and check 914 continue until the appropriate number of data bytes has been summed. When the appropriate number of data bytes has been summed, then a division block 916 divides the sum by the number of data bytes to provide the average. A write block 918 follows which writes the average in the controller's average hold register. The device may write this average to the particular elastic buffer sub-block's average register, another register, a data buffer (see "average as data in" below), and/or the value may be read by the device directly and used for adjusting the stimulation therapy. Thereafter, a continuation block 920 ensures that other tasks continue after averaging has been completed.

An alternative averaging approach, referred to as "average as data in", involves using a previous elastic buffer sub-block's average as a data input. In this approach, a SRAM controller writes the value of the average, located in the SRAM controller's average hold register, to two locations: (i) the average register of the current addressed sub-block's register and (ii) the current data location of the next elastic buffer sub-block's SRAM data buffer. For example, after calculation of the average of elastic buffer sub-block X, the SRAM controller stores the average in the SRAM controller's average hold register and then writes to both the average register of elastic buffer sub-block X and the current SRAM data buffer location of elastic buffer sub-block X+1 (as long as the X+1 sub-block is configured as "average as data in" its configuration register). This process occurs in two consecutive clock cycles. Further, according to this process, the SRAM controller treats the average value as "valid" and, therefore, enters a one in the corresponding validity buffer.

A potential subsequent operation used, for example, in executing a particular fill feature, involves writing the average to the valid or invalid register of an elastic buffer sub-block configured as "average as data in". The SRAM controller stores this value in the valid data in register or invalid data in register but does not propagated the value to the associated SRAM data buffer.

Of course, the SRAM controller optionally includes the ability to avoid certain averaging operations or to minimize the consequences thereof. For example, when one elastic buffer sub-block is configured as "average as data in" but the previous elastic buffer sub-block is not configured to average the data, the SRAM controller ensures that the result will not be written to the buffer configured as "average as data in". In this example, the contents the SRAM controller's average calculate register and average hold register and the associated sub-block average register remain unchanged. Thus, unless the previous elastic buffer sub-block is configured to average, the subsequent elastic buffer sub-block, if configured as "average as data in", is effectively configured as "average off". In addition, for grouped elastic buffer sub-blocks, the SRAM controller generally forbids configuration of the first sub-block of each group as "average as data in".

Fill Feature

Another SRAM controller option includes a data fill feature wherein, for example, the controller propagates a data value to all data storage locations in a data buffer. In one exemplary data fill process, the SRAM controller propagates a data byte from an elastic buffer sub-block valid register or invalid register. According to this process, the SRAM controller checks and/or writes to the configuration register of the particular elastic buffer sub-block. The status of the fill-associated bits of the configuration register determines how the fill process proceeds. Where the process involves writing the same data byte to all storage locations of a 32 byte data buffer, the elastic buffer achieves the fill in 33 clock cycles. If the subsequent elastic buffer sub-block has concatenation on, the fill process propagates the data byte fill value and corresponding validity status to all concatenated elastic buffer sub-block data buffers.

In terms of priority, the fill feature generally takes precedence over other controllable features. For example, for simultaneous configuration of both fill and "average as data in" features, the SRAM controller executes the fill feature first, then once complete, the SRAM controller operates the configured elastic buffer sub-block as "average as data in" on the next operation associated with that elastic buffer sub-block.

Timing Considerations

To perform most of the elastic buffer sub-block operations, the elastic buffer requires, at a minimum, execution of two steps: (i) transfer of firmware/software instruction(s) to the SRAM controller; and (ii) operation of the SRAM controller in association with the SRAM. On the basis of this two-step procedure, many of the elastic buffer sub-block tasks require several clock cycles to execute. For example, a write function with no average, no fill, no concatenation and no "average as data in" feature executes in a minimum of two clock cycles (note that a read function does not require an elastic buffer clock cycle). With concatenation enabled, the elastic buffer requires a number of clock cycles equal to the product of two times the number of concatenated sub-blocks plus one. With "average as data in" enabled, after calculation of the average, the elastic buffer requires an extra clock cycle. Regarding averages, 4, 8, and 16 byte averages require 5, 9, and 17 additional clock cycles, respectively, to determine the average and update an elastic buffer sub-block average register. As for fill, writing to a valid/invalid register and to all fill registers requires a number of clock cycles equal to the product of 32 times the sum of the number of concatenated buffers plus one. As a further example, consider at least two elastic buffer sub-blocks configured for a 4 data byte average and "average as data in". In this example, the elastic buffer requires 7 clock cycles to perform the following four steps: (i) writing a byte of data to the specified elastic buffer sub-block (1 cycle); (ii) calculating the average of the 4 most recent data bytes (4 cycles); inputting the calculated average to the average register of the specified elastic buffer sub-block (1 cycle); and (iv) inputting the average to the subsequent elastic buffer sub-block (1 cycle).

According to an exemplary elastic buffer, a fast clock is used to shift data bytes through the data registers. The fast clock logic is requested by a request signal upon the first data write into an elastic buffer sub-block valid register or invalid register. This signal remains asserted until the busy register signal is de-asserted.

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

The invention claimed is:

1. A method for operating an implantable stimulation device comprising:
    acquiring information about a patient using the implantable stimulation device;
    transmitting the acquired information to a hardware elastic buffer in the implantable stimulation device;
    holding the acquired information in a hardware register of the hardware elastic buffer;
    reading a pointer to determine a memory storage location of the hardware elastic buffer for storing the acquired information held in the hardware register;
    shifting relative addresses of information stored previously in memory storage locations of the hardware elastic buffer;
    storing the acquired information held in the hardware register to the determined memory storage location of the hardware elastic buffer; and
    associating the stored, acquired information with a relative address that indicates that the stored, acquired information is the most recent information stored in the memory storage locations of the hardware elastic buffer, wherein the hardware elastic buffer reduces computational requirements of the implantable stimulation device.

2. The method of claim 1, wherein the storing comprises storing the acquired information to SRAM in the hardware elastic buffer.

3. One or more computer-readable media having computer-readable instructions thereon which, when executed by a programmable stimulation device, cause the stimulation device to execute the method of claim 1.

4. A method for operating an implantable stimulation device, comprising:
    defining an elastic buffer size based on a number of storage locations in a SRAM chip;
    acquiring a piece of information about a patient using the implantable stimulation device;

transmitting the piece of information to a SRAM controller in the implantable stimulation device;

routing the piece of information to a first of the storage locations in the SRAM chip using the SRAM controller, the first storage location initially associated with a first of a number of relative addresses wherein the number of relative addresses equals the number of storage locations;

acquiring an additional piece of information about a patient using the implantable stimulation device;

transmitting the additional piece of information to a SRAM controller in the implantable stimulation device;

shifting the relative address of the previously routed piece of information from the first relative address to a second relative address;

routing the additional piece of information to a second of the storage locations using the SRAM controller; and associating the additional piece of information with the first relative address, wherein the elastic buffer reduces computational requirements of the implantable stimulation device.

5. The method of claim 4, further comprising:

filling the number of storage locations in the SRAM chip by repeating the acquiring, the transmitting, the shifting, the routing, and the associating for yet additional pieces of information; and assigning a pointer to the first storage location to indicate that it contains the oldest piece of information.

6. One or more computer-readable media having computer-readable instructions thereon which, when executed by a programmable stimulation device, cause the stimulation device to execute the method of claim 4.

7. A method for operating an implantable stimulation device comprising:

transmitting an address to a hardware elastic buffer in the implantable stimulation device;

decoding the transmitted address by reading a pointer associated with the hardware elastic buffer and by using an address decoder of the hardware elastic buffer; and retrieving data from a memory storage location of the hardware elastic buffer based on the decoding, wherein the hardware elastic buffer reduces computational requirements of the implantable stimulation device.

8. The method of claim 7, wherein the memory storage location comprises SRAM and the retrieving comprises reading data from the memory storage location using a SRAM controller.

9. The method of claim 8, wherein the retrieving comprises decoding the address using an address decoder in the SRAM controller.

10. One or more computer-readable media having computer-readable instructions thereon which, when executed by a programmable stimulation device, cause the stimulation device to execute the method of claim 7.

11. An implantable stimulation device comprising a hardware elastic buffer wherein the hardware elastic buffer comprises:

a number of memory storage locations;

a pointer configured to point, incrementally, to one of the number of memory storage locations;

an address decoder to associate a received address to one of the number of memory storage locations based in part on the pointer; and hardware registers that comprise at least one hardware register configured to hold data to be written to one of the number of memory storage locations, wherein the hardware elastic buffer reduces computational requirements of the implantable stimulation device.

12. The device of claim 11, wherein said hardware elastic buffer comprises SRAM.

13. The device of claim 12, wherein said hardware elastic buffer further comprises a SRAM controller.

14. The device of claim 13, wherein said SRAM controller comprises an input for receiving information.

15. The device of claim 12, wherein said SRAM comprises a data buffer.

16. The device of claim 12, wherein said SRAM comprises a data validity buffer.

17. The device of claim 11 wherein said hardware registers comprise a valid data in hardware register configured to hold data to be written to one of the number of memory storage locations.

18. The device of claim 11 wherein said hardware registers comprise an invalid data in hardware register configured to hold data to be written to one of the number of memory storage locations.

19. The device of claim 11 wherein said hardware registers comprise a configuration hardware register.

20. The device of claim 11 wherein said hardware registers comprise an average calculate hardware register.

21. The device of claim 11 wherein said hardware registers comprise an average hold hardware register.

22. An implantable stimulation device comprising:

SRAM; and a controller to control the SRAM wherein the controller comprises control logic configured to point a pointer to one of a plurality of storage locations of the SRAM and to shift relative addresses associated with data stored in the plurality of storage locations responsive to a command to write data to the one of the plurality of storage locations associated with the pointer, wherein the SRAM reduces computational requirements of the implantable stimulation device.

23. The device of claim 22, wherein said SRAM controller comprises a plurality of hardware registers.

24. The device of claim 22, wherein said SRAM controller comprises an address decoder.

25. The device of claim 22 further comprising a data averaging feature.

26. The device of claim 22 further comprising a concatenation feature.

27. The device of claim 22 further comprising a fill feature.

28. An implantable stimulation device comprising:

acquiring means for acquiring information about a patient; and storage means for storing the acquired information, said storage means comprising a hardware elastic buffer that comprises control logic configured to point a pointer to one of a plurality of storage locations of the storage means and to shift relative addresses associated with information stored in locations of the storage means responsive to a command to write information to the one of the plurality of storage locations associated with the pointer, wherein the hardware elastic buffer reduces computational requirements of the implantable stimulation device.

29. The device of claim 28 wherein said storage means further comprises SRAM.

30. The device of claim 28 wherein said storage means further comprises a buffer controller.

31. The device of claim 30 wherein said buffer controller comprises a SRAM controller.

32. The device of claim 28 wherein said storage means comprises an address decoder.

33. The device of claim 28 further comprising average means for averaging the acquired information.

34. The device of claim 28 further comprising concatenation means for concatenating the acquired information in a plurality of SRAM chips.

35. The device of claim 28 further comprising fill means for filling a plurality of storage locations in a SRAM chip with a selected value.

36. The device of claim 28 further comprising validity means for tracking validity of the acquired information.

37. The device of claim 28 wherein said storage means comprises a configuration means for configuring said storage means.

38. The device of claim 37 wherein said configuration means comprises a hardware register.

39. A method for operating an implantable stimulation device comprising:

acquiring a piece of information about a patient using the implantable stimulation device;

transmitting the piece of information to a SRAM controller in the implantable stimulation device;

routing the piece of information to a first of a plurality of storage locations in a SRAM chip using the SRAM controller;

repeating the acquiring and the transmitting for another piece of information;

shifting a relative address of the piece of information stored in the first of the plurality of storage locations;

routing the other piece of information to a second of a plurality of storage locations in a SRAM chip using the SRAM controller;

filling the plurality of storage locations by repeating the acquiring, the transmitting, the shifting, and the routing for additional pieces of information;

acquiring yet an additional piece of information using the implantable stimulation device;

transmitting the additional piece of information to the SRAM controller in the implantable stimulation device; and routing the additional piece of information to the first of the plurality of storage locations in a SRAM chip using the SRAM controller to thereby replace the previously acquired piece of information located in the first of the plurality of storage locations, wherein the SRAM reduces computational requirements of the implantable stimulation device.

* * * * *